United States Patent [19]

Hirschbuehler et al.

[11] Patent Number: 4,623,681

[45] Date of Patent: Nov. 18, 1986

[54] CURABLE EPOXY RESIN COMPOSITIONS

[75] Inventors: Kevin Hirschbuehler, Bel Air, Md.; Dalip K. Kohli, Norwalk, Conn.

[73] Assignee: American Cyanamid Company, Stamford, Conn.

[21] Appl. No.: 518,874

[22] Filed: Aug. 1, 1983

[51] Int. Cl.$^4$ ............................................. C08K 3/04
[52] U.S. Cl. .................... 523/468; 523/400; 525/504; 528/124; 528/305
[58] Field of Search ............... 523/468; 528/124, 305; 535/504

[56] References Cited

U.S. PATENT DOCUMENTS 3,932,360  1/1976  Cerankowski et al. ..... 260/77.5 AM

FOREIGN PATENT DOCUMENTS

| 52-74655 | 6/1977 | Japan | 523/468 |
|---|---|---|---|
| 1017612 | 1/1966 | United Kingdom . | |
| 1024288 | 3/1966 | United Kingdom . | |
| 1182377 | 2/1970 | United Kingdom . | |

OTHER PUBLICATIONS

Gillhan, et al., Organic Coatings and Applied Polymer Science Proceedings, vol. 46, pp. 592–598, Mar.–Apr. 1982.
Gillhan, et al., Organic Coatings and Applied Polymer Science Proceedings, vol. 48, pp. 566–570, Mar. 1983.
A.C.A. Symposium Series #114, 1979, p. 157.

Primary Examiner—Lewis T. Jacobs
Attorney, Agent, or Firm—William H. Calnan

[57] ABSTRACT

Curable compositions comprising epoxide prepolymers and polyaminobenzoates, alone, or combined with reinforcements, e.g., graphite fibers, and, optionally modified with second resins. The cured resin fiber matrix compositions exhibit high toughness combined with excellent hot/wet strength.

7 Claims, 2 Drawing Figures

CURABLE EPOXY RESIN COMPOSITIONS

FIELD OF THE INVENTION

This invention relates to improved epoxy resin compositions. In addition, it relates to curable epoxy resin compositions comprising reinforcing filaments and epoxy prepolymers combined with aromatic polyamine curing agents.

CROSS REFERENCE

The following concurrently filed applications are related:

| Serial No. | Applicant(s) |
| --- | --- |
| 518,871 | R. P. Krieger, Jr. |
|  | K. Hirschbuehler |
|  | R. P. Politi |
| 518,872, now abandoned, | D. W. Wang |
|  | J. L. Courter |
|  | D. K. Kohli |
| 518,863 | D. K. Kohli |
| 518,873 | K. Hirschbuehler |
| 518,874 | K. Hirschbuehler |
|  | D. K. Kohli |
| 518,879 | D. R. Draney |
|  | D. K. Kohli |
| 518,856, now U.S. Pat. No. 4,518,786, | D. W. Wang |
|  | D. R. Draney |
| 518,875, now U.S. Pat. No. 4,533,686, | K. Hirschbuehler |

BACKGROUND OF THE INVENTION

Epoxy resin compositions are useful to encapsulate electronic components, and as structural adhesives, and the like. Reinforced epoxy resin composites having high strength to weight ratios have found extensive use in the aircraft and aerospace industries, and in other applications where strength, corrosion resistance and light weight are desirable. For instance, fiber resin matrix materials have replaced aluminum and other metals in primary and secondary structures of modern military and commerical aircraft. Sporting equipment such as tennis rackets and golf clubs have also adopted fiber resin materials successfully.

Epoxy resin compositions and fiber modifications are abundant. Since the advent of fiber resin matrix materials, much effort has been expended in improving their properties and characteristics, including the development of many different curing systems.

Amine and polyamine curing agents have received wide acceptance, but the toxicity, low solubility, high exotherm and variable curing rates seen with the most commonly used amines, such as m-phenylenediamine, 4,4'-diaminodiphenyl methane and 4,4'-diaminodiphenyl sulfone, has made further improvement desirable. In particular, for aircraft structural applications, epoxy resins cured with available curing agents are either too brittle or do not have sufficient strength and stiffness under hot/wet conditions. It is disclosed in U.K. Pat. No. 1,182,377, which is incorporated herein by reference, that certain aromatic polyamines are effective as curing agents for a variety of polyepoxides, and the resulting cured compositions are useful as films, moldings, coatings and glass-reinforced laminates. There is no indication in the properties presented in the U.K. Patent that the curing agents exemplified therein will produce the combination of toughness and strength under hot/wet conditions essential for use in the above-mentioned structural applications.

In U.S. Pat. No. 3,932,360, diamine cured polyurethane products are described, in which the diamines are of the formula, e.g.,

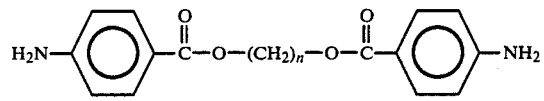

wherein n is an integer from 2 to 12. This '360 patent does not deal with curing compounds having more than one epoxide group per molecule.

In Gillhan et al, Organic Coatings and Applied Polymer Science Proceedings, Vol. 46, p. 592–598, March-April, 1982, polyepoxides cured with diamines of the immediately preceding formula (n is 3), are described.

The present development relates to curable epoxy resin compositions. In one of its aspects, it provides fiber resin matrixes comprising reinforcing filaments in a heat-curable epoxy resin composition comprising an epoxy prepolymer and a novel family of aromatic polyamine curing agents. No member of this novel family of curing agents is specifically exemplified in the U.K. Patent. The invention provides neat resin formulations having, after cure, improved physical properties, e.g., higher elongation and satisfactory hot/wet modulus. The epoxy compositions of the present invention, cured with filaments, exhibit improved interlaminar toughness and residual compression strength after impact, while maintaining compression strength under hot/wet conditions.

SUMMARY OF THE INVENTION

It is an object of the present invention to provide a fiber matrix composition that affords satisfactory compression strength over known matrix formulations, especially under hot/wet conditions, and improved compression strength after impact.

In accordance with the present invention there are provided fiber-reinforced heat-curable epoxy resin compositions comprising:
(i) an epoxy prepolymer or combination of prepolymers having more than one epoxide group per molecule, and
(ii) an amount effective to promote cure of an amine-functional curing agent or combination of curing agents selected from those of the formula:

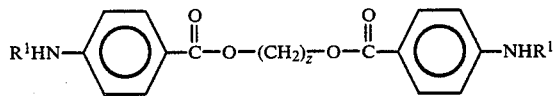

wherein $R^1$ is hydrogen or methyl, and z is an integer of from 2 to 12, preferably 3. Special mention is made of the compound in which $R^1$ is methyl and z is 3. The amount of amine-functional curing agent (b) (ii) should be present in a stoichiometric amount equal to or greater than the epoxy prepolymer (b) (i).

It is among the features of this aspect of the invention to provide such compositions in filled and/or reinforced, e.g., glass fiber reinforced, embodiments which are useful as prepregs, for example, to make laminates and other structural shapes in accordance with procedures known in this art.

DESCRIPTION OF THE PREFERRED EMBODIMENTS

Figure 1:
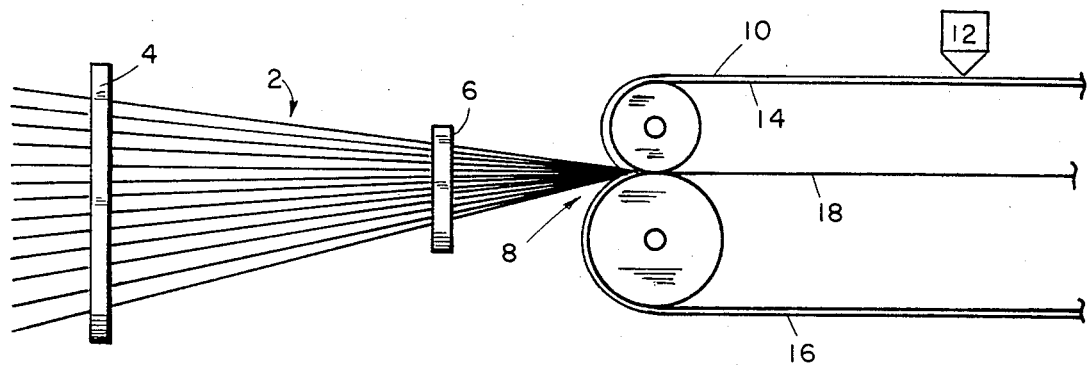
FIG. 1 is a schematic of one method for preparing a fiber resin matrix prepreg tape of the present invention.

In general, the resin compositions of this invention are prepared by mixing the polyepoxide compounds with the polyamines of the above-mentioned formula in conventional quantitative ratios, e.g., 1 epoxide equivalent to 1.0 to 3.0 NH— equivalents, and preferably 1.5 to 2.5 NH— equivalents, optionally with heating, e.g., at a temperature in the range of 30° to 300° C., preferably at a temperature in the range of 80° to 180° C., until a melt is obtained. The melt can then be poured into a mold and reacted, for example, for 2 hours at 135° C. and then for 3 hours at 180° C., to form moldings showing outstanding mechanical and electrical properties. The NH— equivalents is the quantity of aromatic polyamine in grams in which 1 gram-atom of hydrogen combined with amine nitrogen is present.

The fiber resin matrix compositions according to the present invention can be prepared by embedding filaments, e.g., glass fibers and/or non-siliceous filaments in a curable resin composition to form a fiber resin matrix which can be manipulated and cured to a solid composite. Particular selection of the filament material, epoxy prepolymer and curing agent, as well as including optional ingredients such as fillers, dyes, catalysts, processing aids, etc., can give a range of curable compositions heretofore unknown in the art and exhibiting improved physical properties over known materials.

Glass filaments useful herein are well known. The non-siliceous filament component may be of any non-glass, non-silicon dioxide-containing material which improves the strength or other physical properties of the curable epoxy resin component (described infra.). Such filaments include, but are not limited to, filaments comprised of carbon, graphite, silicon carbide, boron, aramid, polyester, polyamide, rayon, polybenzimidazole, polybenzothiazole, metal-coated such filaments, for example, nickel-coated and/or silver-coated graphite fibers and filaments, or combinations of such filaments. Fibers (woven or non-woven), tows or mats of such filaments, or tapes (unwoven, flat bundles of the unidirectional filaments) may be employed as desired. In applications demanding high stiffness to weight ratio or shear strength, carbon fibers, graphite filaments, polyaramid filaments or nickel-plated graphite filaments, as disclosed in assignee's copending application Ser. No. 358,637 are most preferred.

The epoxy resins suitable for the present invention are compounds having more than one epoxide group per molecule available for reaction with the primary and secondary polyamines of the present invention (described infra.). Such epoxy prepolymers include but are not limited to polyglycidyl ethers of polyvalent phenols, for example pyrocatechol; resorcinol; hydroquinone; 4,4'-dihydroxydiphenyl methane; 4,4'-dihydroxy-3,3'-dimethyldiphenyl methane; 4,4'-dihydroxydiphenyl dimethyl methane; 4,4'-dihydroxydiphenyl methyl methane; 4,4'-dihydroxydiphenyl cyclohexane; 4,4'-dihydroxy-3,3'-dimethyldiphenyl propane; 4,4'-dihydroxydiphenyl sulphone; or tris-(4-hydroxyphenyl) methane; polyglycidyl ethers of the chlorination and bromination products of the above-mentioned diphenols; polyglycidyl ethers of novolacs (i.e., reaction products of monohydric or polyhydric phenols with aldehydes, formaldehyde in particular, in the presence of acid catalysts); polyglycidyl ethers of diphenols obtained by esterifying 2 mols of the sodium salt of an aromatic hydroxycarboxylic acid with 1 mol. of a dihalogenoalkane or dihalogen dialkyl ether (U.K. Pat. No. 1,017,612); and polyglycidyl ethers of polyphenols obtained by condensing phenols and long-chain halogen paraffins containing at least 2 halogen atoms (U.K. Pat. No. 1,024,288).

Other suitable compounds include polyepoxy compounds based on aromatic amines and epichlorohydrin, for example N,N'-diglycidyl-aniline; N,N'-dimethyl-N,N'-diglycidyl-4,4'-diaminodiphenyl methane; N,N,N',N'-tetraglycidyl-4,4'-diaminodiphenyl methane; and N-diglycidyl-4-aminophenyl glycidyl ether. Special mention is made of N,N,N',N'-tetraglycidyl-1,3-propylene bis-4-aminobenzoate.

Glycidyl esters and/or epoxycyclohexyl esters of aromatic, aliphatic and cycloaliphatic polycarboxylic acids, for example phthalic acid diglycidyl ester and adipic ester diglycidyl and glycidyl esters of reaction products of 1 mol of an aromatic or cycloaliphatic dicarboxylic acid anhydride and ½ mole of a diol or 1/n mol of a polyol with n hydroxyl groups, or hexahydrophthalic acid diglycidyl esters, optionally substituted by methyl groups, are also suitable.

Glycidyl ethers of polyhydric alcohols, for example of 1,4-butanediol; 1,4-butenediol; glycerol; 1,1,1-trimethylol propane; pentaerythritol and polyethylene glycols may also be used. Triglycidyl isocyanurate; and polyglycidyl thioethers of polyvalent thiols, for example of bis mercaptomethylbenzene; and diglycidyl-trimethylene sulphone, are also suitable.

Preferably the epoxy prepolymer component will be selected from compounds having the idealized formula:

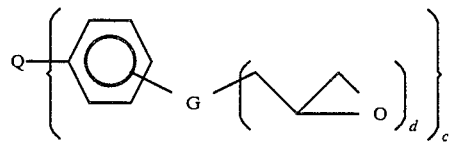

and halogen and alkyl substituted derivatives of such compounds, wherein c is 2, 3 or 4 and equal to the valence of Q; Q is a divalent, trivalent or tetravalent radical; G is —O—, NR'— or

R is hydrogen or alkyl; and d is 1 or 2 depending on the valence of G.

The most preferred epoxy compounds will include the following:

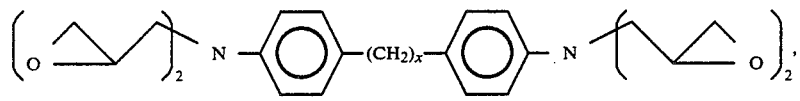

wherein x is an integer from 1 to 4, available commercially (where x=1) as Araldite® MY-720 (Ciba-Geigy);

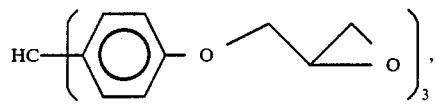

available commercially as XD7342 (Dow Chemical);

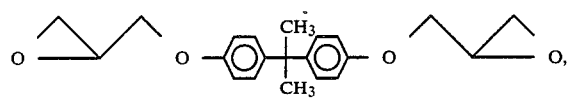

available commercially as DER331 (Dow Chemical) or EPON®828 (Shell);

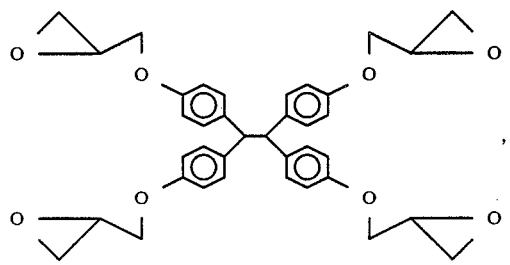

available commercially as EPON®1031 (Shell);

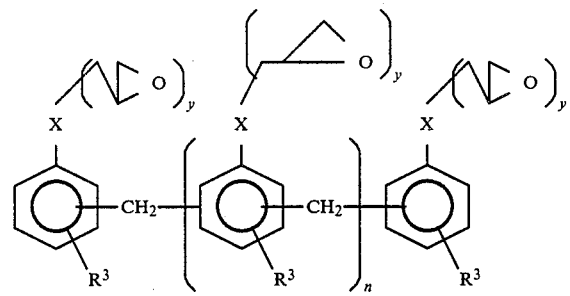

wherein Y is 1 or 2, X is —O— or

$R^3$ is H or $CH_3$ and n is 2 to 8.

Compounds in which X is —O— are available as a mixture under the tradename DEN-438 from Dow Chemical Company.

Also preferred are triglycidyl ethers of meta- and para-hydroxyaniline, e.g., represented by the formula:

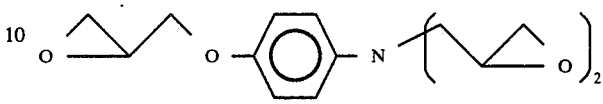

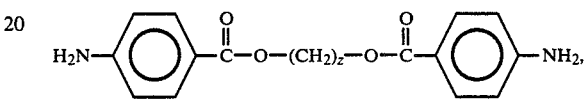

These are available under the tradename ARALDITE®0500, 0510 from Ciba-Geigy.

The polyamine curing agents are of the following formulae:

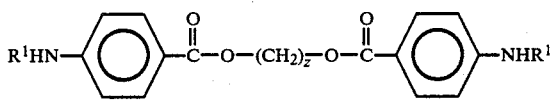

wherein z is an integer of from 2 to 12, preferably 2 to 6.

In the preferred compounds, the primary diamine will include one or more of a compound of the formula:

$$R^1HN-\bigcirc-\overset{O}{\underset{\|}{C}}-O-(CH_2)_z-O-\overset{O}{\underset{\|}{C}}-\bigcirc-NHR^1$$

wherein $R^1$ is hydrogen or $C_1$-$C_6$ alkyl, e.g., methyl, and z is an integer of from 2 to 12, preferably 2 to 6, and most preferably 3. Also contemplated are the use of such compounds in combination with other conventional polyamines such as methylene dianiline, phenylene diamine, 4,4'-diaminodiphenylsulfone and the like.

One method of forming the fiber matrix composition of the invention is illustrated in the drawings. As seen in FIG. 1, the basic fiber matrix material is produced by delivering fiber 2 through conventional eyeboards 4 and 6 to a pressure roller assembly 8. The resin composition is coated in a layer 10 from a conventional film coating applicator 12 onto a substrate such as release paper 14 and passed through the pressure roller assembly 8. Release paper 16 is also delivered to the pressure roller assembly 8.

The pressure rollers 8 are set at a temperature and pressure for imbedding the fibers 2 in the resin layer 10 to form a fiber matrix composition 18. Practice has taught that a temperature in the range of 190° F. and pressures of one thousand pounds over fifteen inch centers are suitable for producing fiber resin prepreg tape 18.

The fibers 2, the substrate 14 with resin layer 10 and the release paper 16 are delivered to the pressure rollers 8 and passed therethrough at the rate of 5–20 feet/minute.

Figure 2:
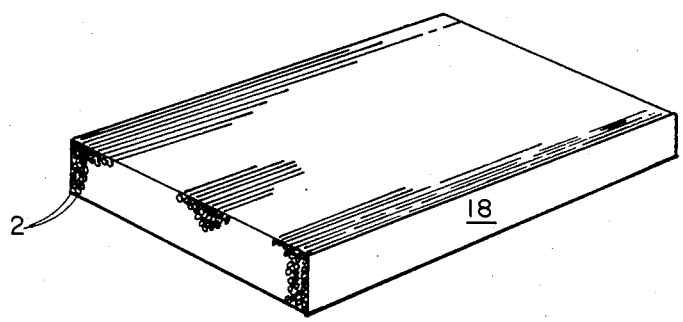
FIG. 2 is an enlarged cross-sectional view of a strip of the fiber resin matrix prepreg tape of the invention.

The feed of fiber 2 and resin layer 10 to the pressure rollers 8 is selected to produce a fiber matrix of about twenty to sixty weight percent resin and about eighty to forty weight percent fiber. For example, one hundred twenty spools of 6K carbon fibers are delivered within a twelve inch width to the pressure rollers 8 with a layer of resin 0.009 to 0.0013 pounds per square foot. The resulting fiber resin matrix 18 results in a generally parallel array of fibers, shown by FIG. 2.

Fillers, pigments, dyes, curing catalysts and other such conventional additives and processing aids may be added to the fiber matrix compositions of the invention before curing to influence the properties of the final resin composite. In addition, polymeric additives such as the butadiene-styrene-acrylonitrile core-shell polymers and the like can be included for their known effects on polymer properties.

The following examples will illustrate the practice of the present invention and are provided by way of demonstration and not by way of limitation.

EXAMPLES 1–3

The following procedure is used to prepare and cure neat resin compositions: the epoxide prepolymer and the polyamine component are mixed at 135° C. for 10 minutes, and cooled to 100° C., the catalyst, if any, is mixed in, and the mixture is degassed for 10 minutes. The liquid resin is then poured into a mold and cured for 2 hours at 135° C. and for 3 hours at 180° C. Properties are determined by the following procedures: The flexural test is described in ASTM D-790, Method I. Dynamic Mechanical Analyzer, and Tg was defined as the temperature at which the loss tangent, tan δ, is a maximum. ASTM D4065 test method covers this type of Tg measurement. Conditioning before testing is described by the phrases "wet" and "dry". "Wet" refers to conditioning for two weeks at 71° C., immersing in distilled water, prior to testing at 93° C. "Dry" means testing a sample, as prepared, at 23° C. The formulations tested and the results obtained are set forth in Table I:

TABLE No. 1

| EPOXY RESIN COMPOSITION AND PROPERTIES | | | | |
|---|---|---|---|---|
| EXAMPLE | | 1 | 2 | 3 |
| COMPOSITION (equivalents) | | | | |
| N,N,N'N'—tetraglycidyl-4,4'-diamino diphenyl methane | | 1.0 | 1.0 | 1.0 |
| N,N'—dimethyl trimethylene bis-(p-aminobenzoate) | | 1.0 | 0.8 | 0.6 |
| PROPERTIES | | | | |
| Modulus, MSI | dry | 0.49 | 0.49 | 0.48 |
|  | wet | 0.19 | 0.22 | 0.25 |
| Strength, KSI | dry | 22.8(y)* | 21.7(y) | 21.9(y) |
| Strain, % | dry | 7.1(y) | 7.1(y) | 7.5(y) |
| Work-to-break, in-lb/in.$^3$ | dry | >1698 | >1600 | >1470 |
| Tg, °C. | dry/wet | 158/120 | 165/— | 163/— |

*(y) = yield

EXAMPLES 4–8

The general procedure of Examples 1–3 was repeated, increasing the ratio of amine equivalents to epoxide equivalents. The formulations used, and the results obtained are shown in Table No. 2:

TABLE No. 2

| INCREASING THE AMINE/EPOXY RATIO | | | | | |
|---|---|---|---|---|---|
| EXAMPLE | 4 | 5 | 6 | 7 | 8 |
| COMPOSITION (equivalents) | | | | | |
| N,N,N',N'—tetraglycidyl-4,4'-diamino diphenyl methane | 1.0 | 1.0 | 1.0 | 1.0 | 1.0 |
| Trimethylene bis(p-aminobenzoate) | 1.0 | 1.25 | 1.5 | 1.75 | 2.0 |
| PROPERTIES | | | | | |
| Modulus, MSI | 0.49 | 0.48 | 0.51 | 0.53 | 0.54 |
| Strength, KSI | 19.0 | 18.8 | 20.4 | 22.7 | 23.1 |
| Strain, % | 4.3 | 4.5 | 4.9 | 5.5 | 5.4 |
| Work-to-break, in-lbs./in$^3$ | 449 | 451 | 560 | 728 | 729 |

The beneficial effect provided by increasing the ratio of amine equivalents to epoxide equivalents is seen from these data.

EXAMPLES 9–14

The general procedures of Examples 1–3 and Examples 4–8 are repeated, including diaminodiphenyl sulfone (DDS) as a co-curing agent and increasing the ratio of the curing agents to epoxide, as was done in Examples 4–8. The formulations used and the results obtained are shown in Table No. 3:

TABLE No. 3

| INCREASING THE AMINE/EPOXY RATIO | | | | | | |
|---|---|---|---|---|---|---|
| EXAMPLE | 9 | 10 | 11 | 12 | 13 | 14 |
| COMPOSITION (equivalents) | | | | | | |
| N,N,N'N'—tetraglycidyl-4,4'-diamino diphenyl methane | 1.0 | 1.0 | 1.0 | 1.0 | 1.0 | 1.0 |
| Diaminodiphenyl sulfone | 0.5 | 0.5 | 0.5 | 0.5 | 0.5 | 0.5 |
| Trimethylene bis-(p-aminobenzoate) | 0.75 | 1.0 | 1.25 | 1.50 | 1.75 | 2.0 |
| PROPERTIES | | | | | | |
| Modulus, MIS | 0.51 | 0.50 | 0.54 | 0.57 | 0.60 | 0.60 |
| Strength, KSI | 20.8 | 21.0 | 23.0 | 27.3 | 26.7 | 29.9 |
| Strain, % | 4.8 | 5.0 | 5.0 | 6.8 | 5.7 | 7.4 |
| Work to break, in.-lb./in.$^3$ | 545 | 592 | 655 | 1156 | 915 | 1476 |

The beneficial effect on properties resulting from an increase in the ratio of amine equivalents to epoxide equivalents again is demonstrated.

The above-mentioned patents, applications and publications are incorporated herein by reference. It is seen that the present invention produces articles of manufacture with beneficial properties, making them useful in a variety of applications. Many variations will suggest themselves to those skilled in this art in light of the foregoing detailed description. All such obvious variations are within the full intended scope of the appended claims.

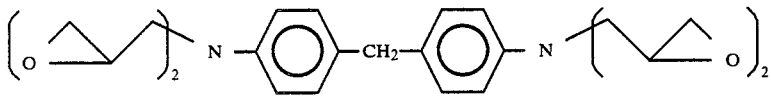

What is claimed is:

1. A fiber resin matrix composition comprised of:
    (a) non-siliceous reinforcing filaments, and
    (b) a heat-curable epoxy resin composition comprising:
        (i) an epoxy prepolymer or combination of prepolymers having more than one epoxide group per molecule, and
        (ii) an amount effective to promote cure of an amine functional curing agent or combination of curing agents selected from esters of the formula:

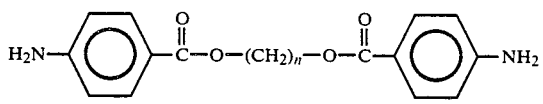

wherein n is an integer of from 2 to 12, the amine-functional curing agent (b) (ii) being present in greater stoichiometric amounts than the epoxy prepolymer (b) (i).

2. A matrix composition as in claim 1 wherein component (b) comprises materials with the following parts by chemical equivalents distribution:
   1.0 epoxide equivalents in component (b) (i); and
   from about 1.0 to about 3.0 amine equivalents in component (b) (ii).

3. A matrix composition as in claim 2 wherein there are present 1.0 epoxide equivalents in component (b) (i), and from about 1.5 to about 2.5 amine equivalents in component (b) (ii).

4. A matrix as in claim 1 wherein the epoxy prepolymer (b) (i) comprises a compound of the formula:

5. A matrix composition as in claim 1 wherein said curing agent (b) (ii) comprises a compound of the formula:

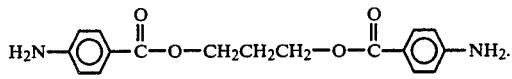

6. A matrix composition as in claim 5 which additionally includes a compound of the formula:

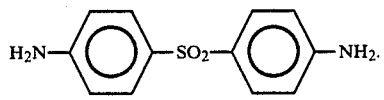

7. A matrix composition as in claim 1 wherein said filaments comprise carbon or graphite filaments.

* * * * *